United States Patent [19]

Foglio et al.

[11] 4,230,619
[45] Oct. 28, 1980

[54] SYNTHETIC ROUTES TO AZETIDINONES RELATED TO NOCARDICIN

[75] Inventors: Maurizio Foglio; Giovanni Franceschi; Paolo Lombardi; Cosimo Scarafile, all of Milan; Federico Arcamone, Nerviano, all of Italy

[73] Assignee: Farmitalia Carlo Erba S.p.A., Milan, Italy

[21] Appl. No.: 921,070

[22] Filed: Jun. 30, 1978

[30] Foreign Application Priority Data

Jul. 5, 1977 [GB] United Kingdom ............... 28193/77

[51] Int. Cl.² .................. C07D 205/08; C07D 513/04
[52] U.S. Cl. .............................. 260/239 A; 260/245.4
[58] Field of Search .................................... 260/239 A

[56] References Cited

U.S. PATENT DOCUMENTS

| | | | |
|---|---|---|---|
| 3,991,069 | 11/1976 | Barton et al. | 260/239 A |
| 4,075,219 | 2/1978 | McShane | 260/239 A |

FOREIGN PATENT DOCUMENTS

| | | |
|---|---|---|
| 2615621 | 10/1976 | Fed. Rep. of Germany . |
| 1519495 | 7/1978 | United Kingdom ................ 260/239 A |

Primary Examiner—Mark L. Berch
Attorney, Agent, or Firm—Stevens, Davis, Miller & Mosher

[57] ABSTRACT

There is disclosed a process for the manufacture of azetidinones related to nocardicin having the formula

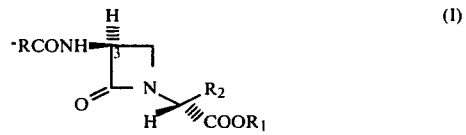

wherein R is a saturated or unsaturated alkyl having from 1 to 6 carbon atoms, α-aminobenzyl, benzyl, free or substituted phenyl, or a free or substituted heterocyclic;

$R_1$ is hydrogen, alkyl having from 1 to 4 carbon atoms, trimethylsilyl, trichloroethyl, benzhydryl or benzyl; and $R_2$ is a free or substituted phenyl, or a free or substituted heterocyclic, using the same starting compound, but with the possibility of proceeding to the final compound via two somewhat different routes. A number of novel intermediates are also disclosed.

1 Claim, No Drawings

SYNTHETIC ROUTES TO AZETIDINONES RELATED TO NOCARDICIN

This invention relates to the manufacture of azetidinone derivatives. More particularly, it relates to a new process for preparing azetidinones which have a remarkable antibiotic activity.

Some of the said azetidinone derivatives are described and claimed in Belgian Pat. No. 830,934 and Dutch Pat. No. 7508008. According to these patents, the novel derivatives have been prepared either from 3-ANA (3-aminonocardicin acid) obtained from fermentation of Nocardia strains, or by a chemical route starting from desthiopenicillins. Both 3-ANA and desthiopenicillins are described in the above-mentioned patents.

The present invention provides a new process for the manufacture of azetidinones related to nocardicin having the formula

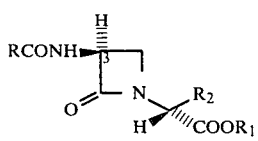

(I)

wherein R is a saturated or unsaturated alkyl having from 1 to 6 carbon atoms, α-aminobenzyl, benzyl, free or substituted phenyl, or a free or substituted heterocyclic;

$R_1$ is hydrogen, alkyl having from 1 to 4 carbon atoms, trimethylsilyl, trichloroethyl, benzhydryl or benzyl; and $R_2$ is a free or substituted phenyl, or a free or substituted heterocyclic.

By "heterocyclic" is meant a 5- or 6-membered ring having one, two or three hetero-atoms in its ring selected from the class consisting of oxygen and nitrogen; and more particularly by way of example, furan, pyridine, pyrazine, pyrrole, imidazole, piperidine, pyrazole, oxadiazole, benzimidazole, quinoline and tetrazole.

The substituents attached to the phenyl and/or the heterocyclic rings are selected from the class consisting of hydroxy, alkoxy, nitro, amino, alkyl and halogens, which if desired may be protected by suitable groups. The alkoxy or alkyl groups preferably are from 1 to 4 carbon atoms.

According to the present invention, a compound of the formula

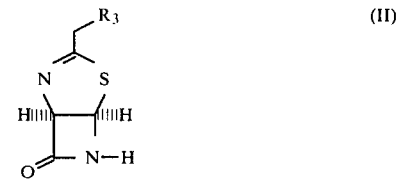

(II)

wherein $R_3$ is phenyl or phenoxy, is reacted with a compound of formula $YCHR_2COOR_1$, in which Y is a suitable leaving group such as iodine, bromine, chlorine, sulphonyloxy, acyloxy, and in which $R_1$ and $R_2$ have the meanings set forth above, in the presence of a metal hydride in a solvent such as anhydrous tetrahydrofuran, dimethylformamide, hexamethylphosphoramide, or their mixtures, at a temperature ranging from $-30°$ to $20°$ C., to give a compound of formula (III).

This reaction takes place with a high degree of stereo-selectivity due to the strictly bent shape of the fused thiazoline (II) which controls the steric orientation in alkylation.

The compound of formula (III) is N-acylated with concomitant shift of the double bond to the extranuclear position to give a thiazolidine (IV). The acylation is performed by a suitable acyl halide RCOX, where X is halogen and R has the meaning stated above, in the presence of an organic base or a saturated aqueous solution of $NaHCO_3$ in a two-phase system.

Hydrolytic cleavage of (IV) with a 2 N aqueous solution of HCl in acetone, or simply by passing through a silica gel column, yields the 4-thioacyl derivative (V) which in turn, after reductive desulphurization with Raney-Ni, affords the azetidinone (I).

A marked advantage of this procedure is the possibility of by-passing the 3-ANA by introducing the desired final side chain R at an early stage of the synthesis.

Alternatively, the compounds (III) may be transformed by an acid catalyzed ring opening (British Pat. No. 1,472,865) into the hydrazinothioderivatives (VI) which then, by reductive desulphurization with Raney-Ni, give the desthio-compounds (VII) (I=VII when $R_3=R$).

While the starting material of this procedure, that is compounds of formula (II), have been described by R. D. G. Cooper and F. L. Jose, JACS, 94, 1021, 1972, synthons (III), (IV), (V) and (VI) are new compounds and are to be regarded as a part of the present invention.

The compounds of formula (I) in which $R_2$ is different from phenyl or substituted phenyl are also new compounds.

It is worthwhile to note that the above compounds can be transformed into the corresponding 3-free-amino compounds by cleavage of the acyl side-chain with phosphorus pentachloride.

Azetidinone analogues of formula (I) wherein the RCONH group in position 3 is replaced by $H_2N$, are also new compounds.

SYNTHESIS DIAGRAM

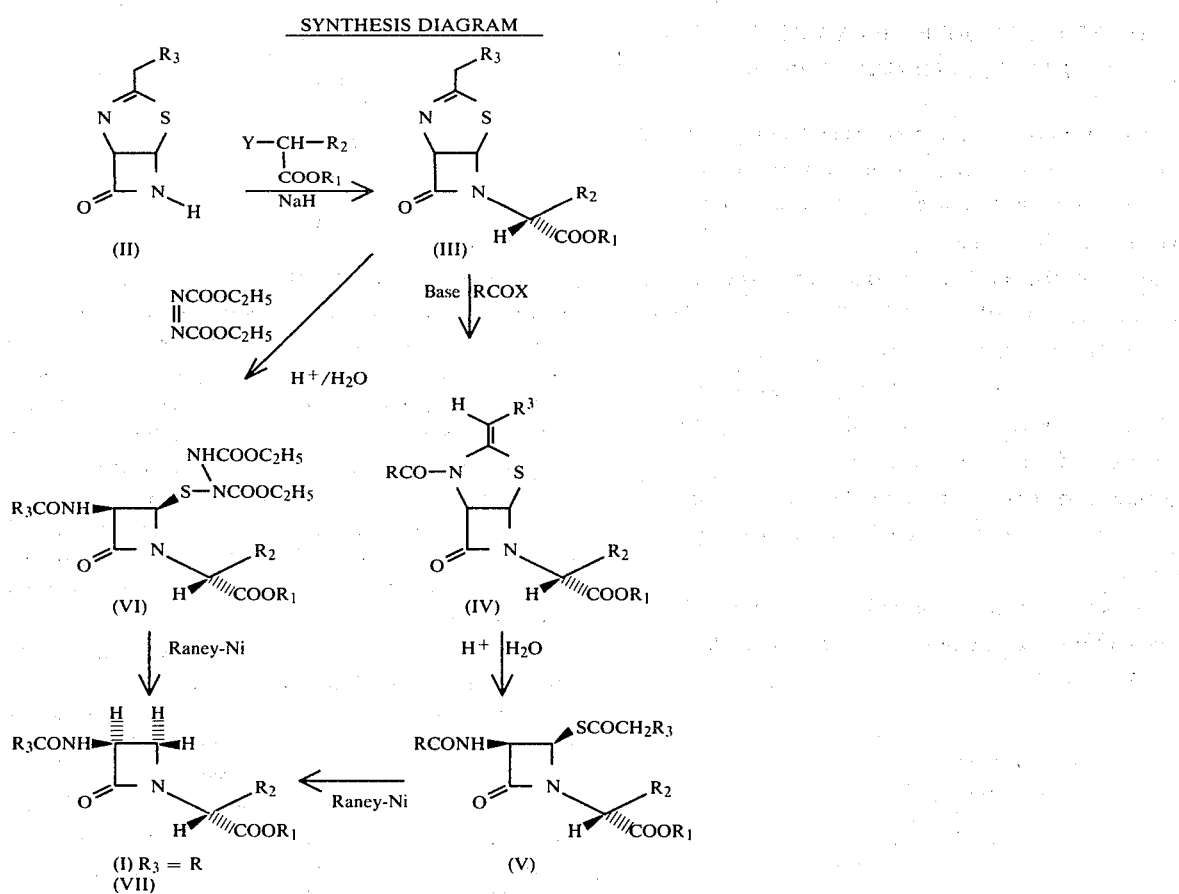

EXAMPLE 1

1α,5α-3-benzyl-4-thia-2,6-diazabicyclo-[3-2-0]-2-heptene-6-(α-methoxy-carbonyl-3-bromo-4-methoxybenzyl)-7-one.

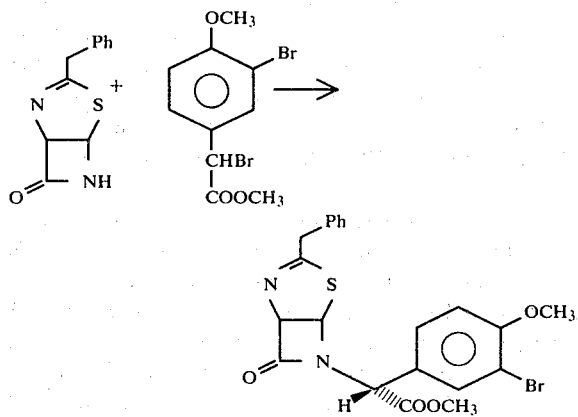

To a suspension of 200 mg of NaH (55% mineral oil dispersion) in 5 ml of anhydrous tetrahydrofuran were added 900 mg of 1α,5α-3-benzyl-4-thia-2,6-diazabicyclo-[3-2-0]-2-heptene-7-one [D. H. R. Barton, J.C.S. Chem. Comm., 1137 (1971)] dissolved in 60 ml of anhydrous tetrahydrofuran, dropwise at 0° C. and under nitrogen atmosphere. After hydrogen evolution ceased, stirring was continued for a further 15 minutes.

To the resulting orange-brown solution were added 1.16 g of (±)-α-bromo-(3-bromo-4-methoxy)phenyl acetic acid methyl ester dissolved in 10 ml of anhydrous tetrahydrofuran, in a dropwise manner at 0° C. After the addition was completed, stirring was continued for a further 60 minutes.

The reaction mixture was then quenched by adding 100 ml of cold water, followed by 10 ml of 1N HCl solution.

The aqueous phase was extracted with ethyl acetate, the combined extracts were washed to neutral with saturated NaCl solution, and dried on $Na_2SO_4$.

Evaporation of the solvent in vacuo yielded a residue which was chromatographed on silica gel. Elution with 5% AcOEt-$C_6H_6$ gave the title product in satisfactory yield.

P.M.R. ($CDCl_3$): 3.77δ(s, $CH_3O$), 3.86δ(s, $CH_3O$ and $CH_2$), 5.43δ(s, exocyclic C-H), 5.70–6.06δ(m, β-lactam protons), 6.90–7.70δ(m, aromatic protons).

EXAMPLE 2

1α,5α-3-Benzyl-4-thia-2,6-diazabicyclo-[3-2-0]-2-heptene-6-(α-methoxy-carbonyl-benzyl)-7-one was prepared by a procedure similar to that given in Example 1.

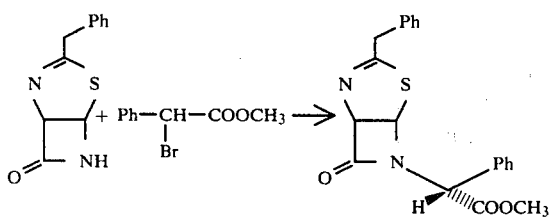

$[\alpha]_D = -175°$ (CHCl$_3$).

P.M.R. (CDCl$_3$): 3.74δ(s, CH$_3$O and —CH$_2$—), 5.57δ(s, exocyclic CH), 5.75–6.05δ(m, β-lactam protons), 6.9–7.5δ(m, aromatic protons).

EXAMPLE 3

1α,5α-3-Benzyl-4-thia-2,6-diazabicyclo-[3-2-0]-2-heptene-6-(α-ethoxy-carbonyl-benzyl)-7-one was prepared by a procedure similar to that given in Example 1.

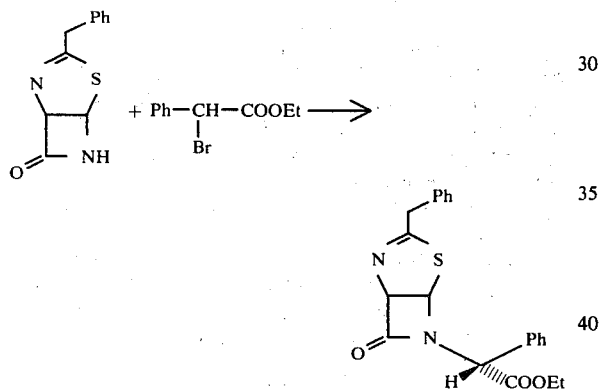

P.M.R. (CDCl$_3$): 1.23δ(t,<u>CH$_3$</u>—C H$_2$), 3.74δ(s, <u>CH$_2$</u>—C$_6$H$_5$), 4.20δ(q, <u>CH$_2$</u>—C H$_3$), 5.50δ(s, exocyclic C—H), 5.65–6.05δ(m, β-lactam protons), 6.9–7.5δ(m, aromatic protons).

EXAMPLE 4

1α,5α-3-benzylidene-2-phenylacetyl-4-thia-2,6-diazabicyclo-[3-2-0]-heptane-6-(β-methoxy-carbonyl-benzyl)-7-one.

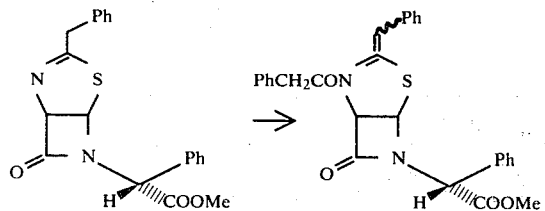

A solution of 800 mg of 1α,5α-3-benzyl-4-thia-2,6-diazabicyclo-[3-2-0]-2-heptene-6-(α-methoxycarbonyl-benzyl)-7-one in 40 ml of dichloromethane was stirred with 30 ml of a saturated aqueous solution of NaHCO$_3$.

To the foregoing mixture were added 1.3 ml of phenylacetylchloride in a dropwise manner at 0° C. After 30 minutes, the organic phase was separated and washed with a saturated NaCl solution, dried on Na$_2$SO$_4$ and evaporated in vacuo to give the crude thiazolidine which was subjected to further transformations without any purification.

EXAMPLE 5

1α,5α-2-phenylacetyl-3-benzylidene-4-thia-2,6-diazabicyclo-[3-2-0]-heptane-6-(α-methoxy-carbonyl-3-bromo-4-methoxybenzyl)-7-one was prepared by a procedure similar to that given in Example 4.

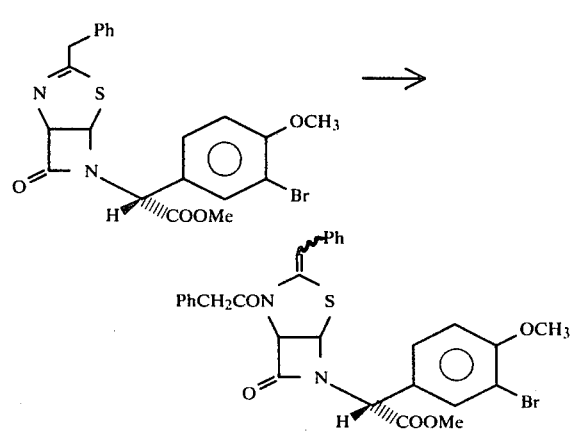

P.M.R. (CDCl$_3$): 3.60δ(s, CH$_2$), 3.63δ(s, CH$_3$O), 4.05δ(s, CH$_3$O), 5.35δ(s, exocyclic C—H), 5.70–6.40δ(m, β-lactam protons), 6.53δ(s, olefinic proton), 6.60–7.60δ(m, aromatic protons).

EXAMPLE 6

1-(α-methoxycarbonyl-benzyl)-3-phenyl-acetamido-4-phenylacetyl-thio-2-azetidinone.

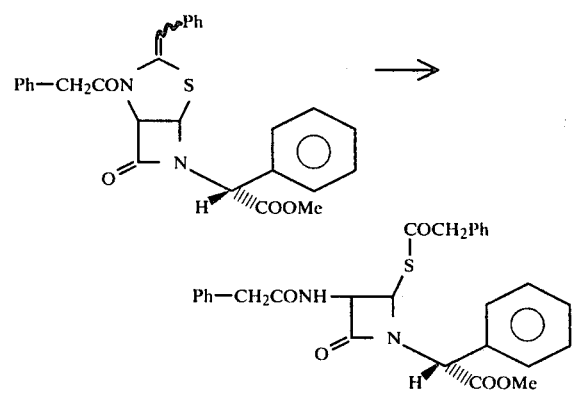

A mixture of 800 mg of 1α,5α-2-phenylacetyl-3-benzylidene-4-thia-2,6-diazabicyclo-[3-2-0]-2-heptane-6-(α-methoxycarbonylbenzyl)-7-one in 50 ml of acetone and 10 ml of 2N aqueous solution of HCl was stirred at room temperature during 8 hours. The solution was then diluted with water and extracted with ethyl acetate. The combined extracts were washed with saturated NaHCO$_3$ solution, with saturated NaCl solution, and then dried on Na$_2$SO$_4$.

The solvent was evaporated in vacuo to yield a solid which was crystallized from Et$_2$O.

P.M.R. (CDCl₃): 3.50 and 3.56δ(two s, 2CH₂), 3.78δ(s, CH₃O), 5.25–5.60δ(m, C—3—H and exocyclic CH), 5.95δ(d, C—4—H), 6.53δ(d, NH), 7.05–7.70δ(m, aromatic protons).

EXAMPLE 7

1-(α-ethoxycarbonylbenzyl)-3-phenylacetamido-4-phenylacetylthio-2-azetidinone was prepared by a procedure similar to that given in Example 6.

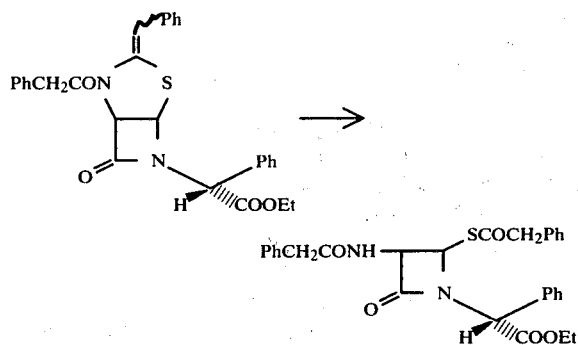

P.M.R. (CDCl₃): 1.23δ(t, $\underline{CH_3}$—C H₂), 3.44δ(s, 2 CH₂), 4.20δ(q, $\underline{CH_2}$—C H₃), 5.25–5.55δ(m, C—3—H and exocyclic C—H), 5.90δ(d, C—4—H), 6.4–8.1δ(m, NH and aromatic protons).

I.R. (CHCl₃): 1778 cm⁻¹ υ C═O β-lactam 1744 cm⁻¹ υ C═O ester 1690 cm⁻¹ υ C═O thioester and amide.

EXAMPLE 8

1-(α-methoxycarbonyl-3-bromo-4-methoxybenzyl)-3-phenyl-acetamido-4-phenylacetylthio-2-azetidinone was prepared by a procedure similar to that given in Example 6.

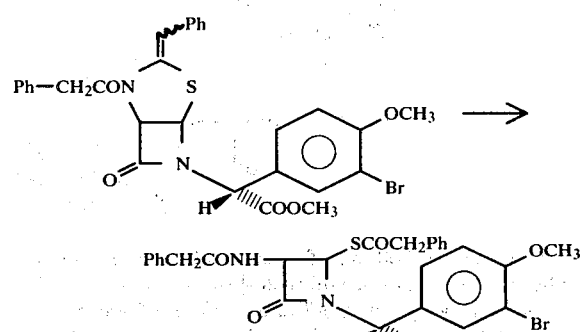

P.M.R. (CDCl₃): 3.46δ(s, 2 CH₂), 3.68 and 3.85δ(two s, CH₃O), 5.2–5.5δ(m, C—3—H and exocyclic C—H), 5.80δ(d, C—4—H), 6.08δ(d, NH), 6.9–7.6δ(m, aromatic protons).

EXAMPLE 9

1-(α-methoxycarbonylbenzyl)-3-phenylacetamido-4-N,N'-diethoxycarbonyl-hydrazinthio-2-azetidinone.

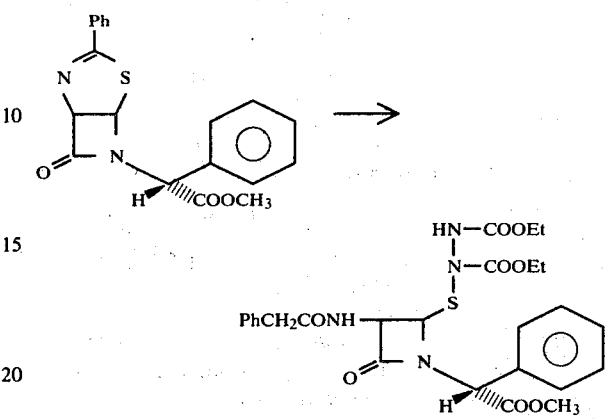

A mixture of 600 mg of 1α,5α-3-benzyl-4-thia-2,6-diazabicyclo-[3-2-0]-2-heptene-6-(α-methoxycarbonylbenzyl)-7-one, 0.4 ml of ethyl azodicarboxylate, 0.2 ml of water, and 150 mg of p-toluenesulphonic acid in 5 ml of acetone was allowed to stand at room temperature over a period of three hours.

The reaction mixture was neutralized with a saturated solution of NaHCO₃ and extracted with ethyl acetate. The combined extracts were washed with saturated NaCl solution, dried on NaSO₄, and evaporated in vacuo to yield a crude product which was purified by column chromatography on silica gel.

Elution with 20% ethyl acetate-benzene gave the title compound in 50% yield.

P.M.R. (CDCl₃): 0.9–1.3δ(m,2 ($\underline{CH_3}$—CH₂—), 3.47δ(s, —CH₂—CO), 3.64δ(s, CH₃O), 4.95–5.57δ(m, C—3—H, C—4—H and exocyclic C—H), 6.40–7.66δ(m, NH and aromatic protons).

EXAMPLE 10

1-(α-methoxycarbonyl-3-bromo-4-methoxybenzyl)-3-phenylacetamido-2-azetidinone.

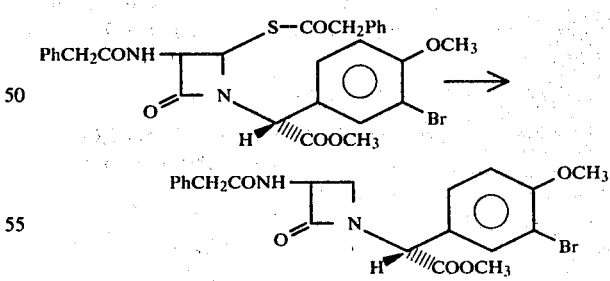

A solution of 700 mg of 1-(α-methoxycarbonyl-3-bromo-4-methoxybenzyl)-3-phenylacetamido-4-phenylacetylthio-2-azetidinone in 80 ml of ethyl acetate and 5 g of Raney-Ni were stirred under hydrogen atmosphere (2.280×10³Torr) over three hours.

After filtration and evaporation of the solvent, the crude product was purified by column chromatography on silica gel.

Elution with 20% ethyl acetate-benzene yielded the title compound (50% yield).

P.M.R. (CDCl₃): 3.07δ(m, C—4—H'), 3.50δ(s, CH₂), 3.74 and 3.90δ(two s, CH₃O), 3.3–4.0δ(m, C—4—H''), 4.86δ(m, C—3—H), 5.50δ(s, exocyclic CH), 6.50δ(d, NH), 6.80–7.60δ(m, aromatic protons).

I.R. (KBr): 1755 cm⁻¹ (νC═O β-lactam and ester) 1675 cm⁻¹ (νC═O amide)
[α]_D= −170° (MeOH).

EXAMPLE 11

1-(α-methoxycarbonylbenzyl)-3-phenylacetamido-2-azetidinone was prepared by a procedure similar to that given in Example 10.

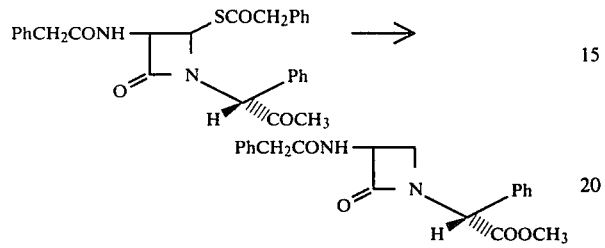

[α]_D= −155° (MeOH)
M.p.: 143° C.
P.M.R. (CDCl₃): 3.06δ(dd, C—4—H'), 3.54δ(d, CH₂), 3.77δ(s, CH₃O) 3.60–4.16δ(m, C—4—H''), 4.96δ(m, C—3—H), 5.63δ(s, exocyclic CH), 6.60δ(d, NH), 7.05–7.70δ(m, aromatic protons).

I.R. (CHCl₃): 1750 cm⁻¹ ν C═O β-lactam and ester 1670 cm⁻¹ ν C═O amide.

EXAMPLE 12

1-(α-methoxycarbonyl-benzyl)-3-phenylacetamido-2-azetidinone was prepared by a procedure similar to that given in Example 11.

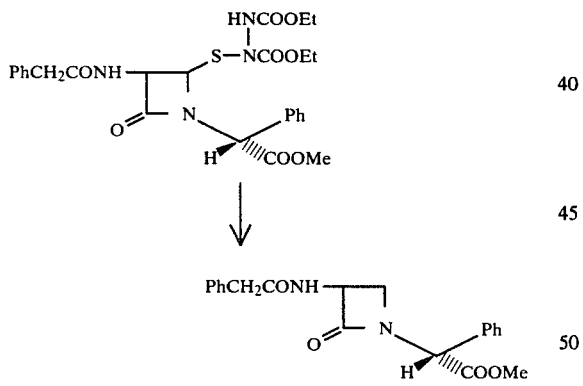

The product is identical in all respects to the product described in Example 11.

What is claimed is:
1. A process for the manufacture of an azetidinone related to nocardicin having the formula (I):

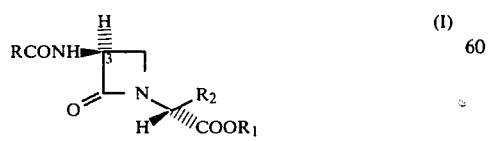

wherein R is a saturated or unsaturated alkyl having from 1 to 6 carbon atoms, α-aminobenzyl, benzyl, a free or substituted phenyl, the phenyl substituent being selected from hydroxy, methyl, methoxy, and amino;

R₁ is hydrogen, alkyl having from 1 to 4 carbon atoms, trimethylsilyl, trichloroethyl, benzhydryl, or benzyl; and R₂ is a free or substituted phenyl, the phenyl substituent being selected from hydroxy, methyl, methoxy, and amino; comprising the steps of (a) reacting a compound of the formula (II):

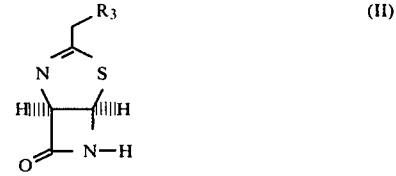

wherein R₃ is phenyl or phenoxy,
with a compound of formula YCHR₂COOR₁, in which Y is a leaving group selected from the group consisting of iodine, bromine, chlorine, acyloxy, and sulphonyloxy, and in which R₁ and R₂ have the meanings set forth above; in the presence of a metal hydride in a solvent selected from the group consisting of anhydrous tetrahydrofuran, dimethylformamide, hexamethylphosphoramide, and their mixtures, at a temperature ranging from −30° to 20° C., to give a compound of the formula (III):

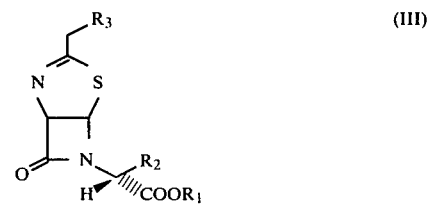

(b) N-acylating the compound of formula (III), with concomitant shifting of the double bond to the extra-nuclear position, by reaction with an acyl halide RCOX, where X is halogen and R has the meaning stated above, in the presence of an organic base or a saturated aqueous solution of NaHCO₃ in a two-phase system, thereby giving a compound of formula (IV):

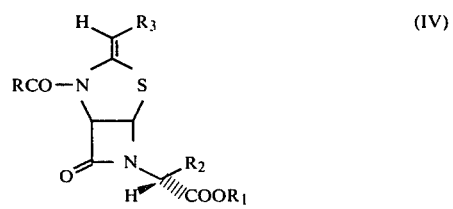

(c) hydrolytically cleaving the compound of formula (IV) by treatment with an aqueous solution of HCl in acetone, or by passing same through a silica gel column, thereby obtaining the 4-thioacyl derivative of formula (V):

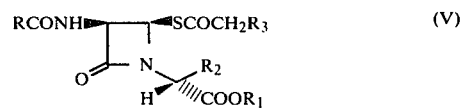

(d) and reductively desulphurizing the compound of formula (V) with Raney-Ni to yield the azetidinone (I).

* * * * *

UNITED STATES PATENT AND TRADEMARK OFFICE
CERTIFICATE OF CORRECTION

PATENT NO. : 4,230,619  
DATED : October 28, 1980  
INVENTOR(S) : Maurizio Foglio, Giovanni Franceschi, Paolo Lombardi, Cosimo Scarafile, Federico Arcamone Page 1 of 2

It is certified that error appears in the above-identified patent and that said Letters Patent are hereby corrected as shown below:

Column 5; Example 4 should read as follows:

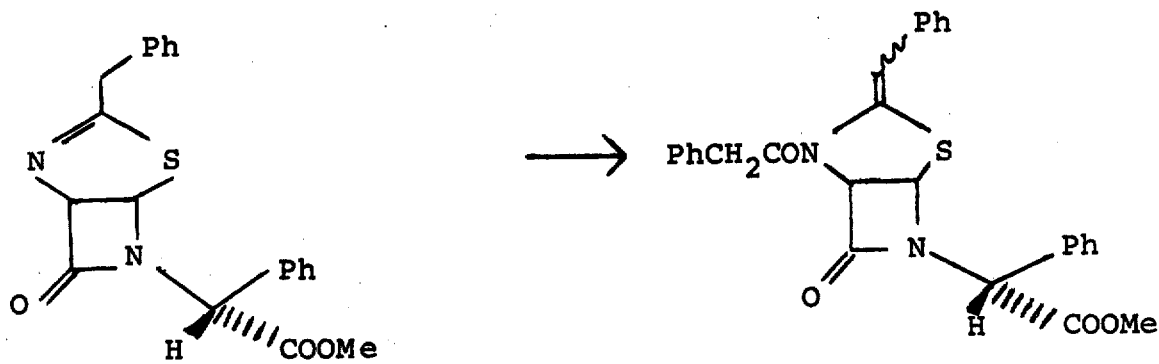

Column 8; Example 9, second line, please change the spelling of "hydrazinthio" to --hydrazinothio--;

UNITED STATES PATENT AND TRADEMARK OFFICE
CERTIFICATE OF CORRECTION

PATENT NO. : 4,230,619

DATED : October 28, 1980

INVENTOR(S) : Maurizio Foglio, Giovanni Franceschi, Paolo Lombardi, Cosimo Scarafile, Federico Arcamone It is certified that error appears in the above-identified patent and that said Letters Patent are hereby corrected as shown below:

Column 9, Example 11, the formula should read as follows:

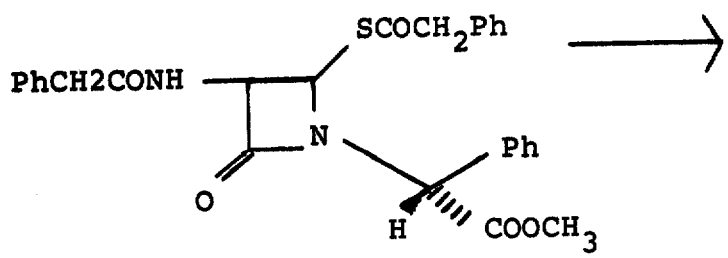

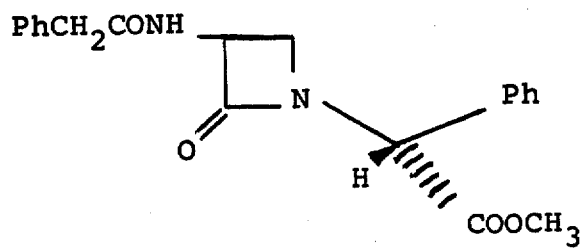

Signed and Sealed this

Fourteenth Day of April 1981

[SEAL]

Attest:

RENE D. TEGTMEYER

Attesting Officer     Acting Commissioner of Patents and Trademarks